(12) United States Patent
Maciejewski

(10) Patent No.: US 11,389,128 B2
(45) Date of Patent: Jul. 19, 2022

(54) MEDICAL IMAGING APPARATUS HAVING AN ADJUSTABLE USER INTERFACE ACCOMMODATED IN AN INDENTATION OF A HOUSING APPARATUS

(71) Applicant: Siemens Healthcare GmbH, Erlangen (DE)

(72) Inventor: Bernd Maciejewski, Markt Erlbach (DE)

(73) Assignee: Siemens Healthcare GmbH, Erlangen (DE)

(*) Notice: Subject to any disclaimer, the term of this patent is extended or adjusted under 35 U.S.C. 154(b) by 408 days.

(21) Appl. No.: 15/935,487

(22) Filed: Mar. 26, 2018

(65) Prior Publication Data

US 2018/0271463 A1    Sep. 27, 2018

(30) Foreign Application Priority Data

Mar. 27, 2017    (DE) .......................... 102017205145.0

(51) Int. Cl.
*A61B 6/00*    (2006.01)
*A61B 5/055*    (2006.01)
(Continued)

(52) U.S. Cl.
CPC ............. *A61B 6/46* (2013.01); *A61B 5/055* (2013.01); *A61B 6/462* (2013.01); *G01R 33/283* (2013.01); *G01R 33/307* (2013.01); *G01R 33/546* (2013.01); *G01T 1/2985* (2013.01); *A61B 2560/0406* (2013.01); *A61B 2560/0487* (2013.01)

(58) Field of Classification Search
CPC ........... A61B 6/46; A61B 6/462; A61B 5/055; A61B 2560/0406; A61B 2560/0487; A61B 6/03; G01R 33/546; G01R 33/283; G01R 33/307; G01T 1/2985; F16M 11/04; F16M 11/08; F16M 11/12; H05K 7/12; H05K 7/14; G06F 1/1601
See application file for complete search history.

(56) References Cited

U.S. PATENT DOCUMENTS 6,317,618 B1    11/2001    Livni et al.
6,550,739 B1 *  4/2003    Brindisi ............... A47G 1/1613
                                                248/476
(Continued)

FOREIGN PATENT DOCUMENTS

CN    110139606 A  *  8/2019    ............. A61B 6/025
DE    102014217487 A1  *  12/2015    ............. A61B 6/00
JP    2012051684 A  *  3/2012    ............. B66C 1/66

OTHER PUBLICATIONS

Berg, Dennis G. "The Basics of Shoulder Screws." Nov. 3, 2011. Machine Design—Fastening & Joining. (Year: 2011).*
(Continued)

*Primary Examiner* — Christopher Koharski
*Assistant Examiner* — Richmond J Van Winter
(74) *Attorney, Agent, or Firm* — Banner & Witcoff Ltd.

(57) ABSTRACT

A housing apparatus for a medical imaging apparatus has at least one housing shell, a substructure support, on which the at least one housing shell can be fastened, and a user interface having a carrier frame and a communication circuit. The carrier frame is arranged on the substructure support so as to be movable in at least one direction.

30 Claims, 4 Drawing Sheets

(51) Int. Cl.
*G01R 33/28* (2006.01)
*G01R 33/30* (2006.01)
*G01R 33/54* (2006.01)
*G01T 1/29* (2006.01)
*A61B 6/03* (2006.01)

(56) References Cited

U.S. PATENT DOCUMENTS

| | | | | |
|---|---|---|---|---|
| 7,866,615 | B2* | 1/2011 | Hsuan | F16M 13/00 |
| | | | | 248/920 |
| 10,835,190 | B2* | 11/2020 | Gregerson | A61B 6/4405 |
| 2004/0155167 | A1* | 8/2004 | Carter | A61C 19/00 |
| | | | | 248/921 |
| 2009/0021901 | A1* | 1/2009 | Stothers | F16M 11/18 |
| | | | | 361/679.27 |
| 2009/0178255 | A1* | 7/2009 | Maciejewski | B60R 13/04 |
| | | | | 24/697.1 |
| 2013/0200896 | A1* | 8/2013 | Maciejewski | G01R 33/3802 |
| | | | | 324/318 |
| 2013/0234709 | A1 | 9/2013 | Hierl et al. | |
| 2016/0096567 | A1* | 4/2016 | Kineses | B62D 65/18 |
| | | | | 269/56 |
| 2016/0174914 | A1* | 6/2016 | Lerch | A61B 6/462 |
| | | | | 5/601 |
| 2017/0350469 | A1* | 12/2017 | Aro | H05K 5/0008 |

OTHER PUBLICATIONS

Webpage for Trak-Kit product. Accessed via internet on Mar. 16, 2022. Publicly available as early as Jun. 10, 2006, as demonstrated by attached copy from Wayback Machine. 2006. http://www.trak-kit.com/#product (Year: 2006).*

* cited by examiner

MEDICAL IMAGING APPARATUS HAVING AN ADJUSTABLE USER INTERFACE ACCOMMODATED IN AN INDENTATION OF A HOUSING APPARATUS

BACKGROUND OF THE INVENTION

Field of the Invention

The present invention concerns a housing apparatus, in particular for a medical imaging apparatus, having at least one housing shell, a substructure support, on which the at least one housing shell can be fastened, and a user interface having a carrier frame and a communication circuit.

Description of the Prior Art

Medical imaging apparatuses such as magnetic resonance apparatuses have a user interface that includes a communication circuit, for example in the form of an input element and/or an output element, such as a display or a control panel. This user interface, in particular the communication circuit, is often integrated in a housing apparatus of the medical imaging apparatus.

If the housing apparatus has a multi-layer structure, the integration of a user interface is particularly difficult, since tolerances of a number of components have to be compensated when integrating the user interface inside the housing apparatus.

DE 10 2012 201 485 A1 describes a medical imaging apparatus with a housing unit having a cladding shell.

Furthermore, DE 10 2011 082 402 B4 discloses a magnetic resonance apparatus having a multi-layer housing unit.

SUMMARY OF THE INVENTION

An object of the present invention is to provide simple integration of a user interface in a housing apparatus, in particular during assembly of the housing apparatus.

The basis of the invention is a housing apparatus, in particular for a medical imaging apparatus, having at least one housing shell, a substructure support, on which the at least one housing shell is fastened, and a user interface having a carrier frame and a communication circuit.

In accordance with the invention the carrier frame is mounted on the substructure support so as to be movable in at least one direction.

The housing apparatus is preferably designed for covering a medical imaging apparatus, such as the scanner of a magnetic resonance apparatus, the scanner of a PET (Positron Emission Tomography) apparatus, the gantry of a computed tomography apparatus, etc. The housing apparatus preferably has a housing portion and/or a covering for the front side of the medical imaging apparatus since integration of a user interface at that location for information exchange with a user, for example a medical operator in charge of the medical imaging examination, is especially expedient. Furthermore, the housing apparatus can have additional covering components and/or housing shells, which seem expedient to those skilled in the art.

The housing apparatus can have a multi-layer structure. An outer layer of the multi-layer housing apparatus is preferably arranged on a side of the housing apparatus remote from the imaging device to be covered, and can form the housing shell. The outer layer and/or the housing shell can also be a design element and/or a design shell of the housing apparatus. An inner layer of the multi-layer housing apparatus can form the substructure support, which is preferably facing the medical imaging apparatus to be covered. The substructure support is designed for fastening the housing apparatus to the medical imaging apparatus.

The user interface preferably has a structural component, which includes the carrier frame as well as the communication circuit. During assembly of the carrier frame inside the housing apparatus, the communication circuit is therefore also mounted inside the housing apparatus. A two-part design of the user interface can also be provided in an alternative embodiment of the invention. The communication circuit is arranged on the carrier frame. Furthermore, the carrier frame is typically provided for mounting the communication circuit on further components, such as the substructure support. The communication circuit can be provided solely for emitting and/or displaying information and/or data, such as being designed as a display and/or as a monitor. The communication circuit is particularly advantageously also provided for entering information and/or data, for example, designed as a touch display and/or a touchscreen. Furthermore, the communication circuit can be designed solely for entering information being designed as a control panel and/or keyboard.

After arrangement and/or fastening on the substructure support, the carrier frame is movable in at least one direction with respect to the substructure support. The carrier frame is preferably arranged and/or fastened on the substructure support so as to be movable in at least two directions with respect to the substructure support. Movement of the carrier frame with respect to the substructure support can be limited by the construction, so that only a defined path length in at least one direction, preferably in two directions, is available for movement of the carrier frame with respect to the substructure support.

For assembly of the housing apparatus, first the substructure support is arranged and/or fastened on the medical imaging apparatus. The user interface is then arranged on and/or fastened on the substructure support by arrangement and/or fastening of the carrier frame on the substructure support. The housing shell is then arranged on and/or fastened on the substructure support. The housing shell preferably has an opening conforming to the user interface, so that in an assembled state of the housing shell, the user interface, in particular the communication circuit of the user interface, is placed inside the opening of the housing shell.

The present invention has the advantage that simple assembly of the housing apparatus with an integrated user interface is achieved. This allows simple and fast integration of the user interface inside the housing apparatus. Due to the movable arrangement of the carrier frame on the substructure support, a compensating movement of the carrier frame, and therewith of the user interface, with respect to the housing shell and/or the substructure support is possible upon final assembly of the housing shell. The compensating movement is a movement that the carrier frame experiences upon assembly of the housing shell on the substructure support, so that the user interface, in particular the communication circuit of the user interface, is placed inside the opening of the housing shell.

As a result, tolerances, such as manufacturing tolerances, of the individual components can advantageously be compensated in the assembly of the user interface and housing shell. Time-consuming individual handling and/or orientation of the user interface and/or housing shell, which take(s) account of the exact and/or individual dimensions of the user interface and/or housing shell, is therefore no longer required in the assembly of the housing apparatus. Even in a service case, in which the housing apparatus has to be disassembled, simple and fast disassembly and assembly of the housing shell can be done by the service technician.

In an embodiment of the invention, the housing apparatus has at least one first fastening element, which provides a pendulum-like support of the carrier frame on the substructure support. Pendulum-like support of the carrier frame means suspension of the carrier frame like a pendulum on the substructure support. The at least one first fastening element preferably forms a pendulum rod, having a free end at which the carrier frame is arranged. The carrier frame is rotatably mounted about an axis, which is preferably arranged outside of the center of mass of the carrier frame. The at least one fastening element for use inside a medical imaging apparatus, in particular a magnetic resonance device, is preferably formed from stainless steel and/or brass. This embodiment of the invention has the advantage that the user interface can be easily fastened and/or arranged on the substructure support since firstly the carrier frame can be arranged on the substructure support by the at least one first fastening element and is therefore secured against dropping in the further assembly of the housing apparatus. Further fastening of the user interface and/or carrier frame can then occur.

The at least one first fastening element preferably is an eyebolt. An eyebolt, in the direction of its longitudinal extent, has a thread at a first end region and a ring at a second opposite end region. The ring of the eyebolt preferably encloses a mounting region with its ring surface, so a surface normal of the ring surface is oriented perpendicularly to the longitudinal extent of the eyebolt. The carrier frame can be supported particularly easily in a pendulum-like manner inside the mounting region enclosed by the ring of the eyebolt. Furthermore, a spacing and/or a position of the carrier frame in the direction of the longitudinal extent of the eyebolt can be adjusted with the thread of the eyebolt.

In another embodiment of the invention, the carrier frame has at least one support element and the at least one first fastening element has a support element corresponding to the support element of the carrier frame, wherein the carrier frame is supported on the at least one first fastening element by the two support elements. The support element of the carrier frame is preferably arranged on a side remote from the communication circuit, in particular a rear side, of the carrier frame. The support element of the carrier frame can extend away from carrier frame. The support element can be arranged on the carrier frame perpendicularly to the surface of the carrier frame having the largest extent. The support element of the carrier frame preferably is cone-like or rod-like in design. The support element of the at least one first fastening element preferably has a support component, such as a ring of an eyebolt. One advantage of this embodiment of the invention is that simple and fast support and/or suspension of the user interface on the substructure support is achieved by introducing the cone-like or rod-like support elements of the carrier frame into the annular support element of the at least one first fastening element.

According to the invention, the substructure support has at least one indentation in which the at least one first fastening element is supported. The at least one first fastening element thus is supported and/or arranged particularly compactly on the substructure support. Furthermore, undesirable hindering of the assembly process involving further components, due to a protruding first fastening element, is prevented. The indentation preferably has a depth that corresponds to a thickness and/or a diameter of the at least one first fastening element, or is greater than the thickness and/or the diameter of the at least one first fastening element, so that the at least one first fastening element can be arranged and/or supported almost completely inside the indentation of the substructure support.

Furthermore, the substructure support can have at least one further fastening element for fastening the at least one first fastening element on the substructure support. Secure support and/or arrangement of the at least one first fastening element on the substructure support is achieved thereby. The further fastening element preferably is a cable tie, which is guided through recesses in the substructure support. This enables particularly inexpensive fastening of the at least one first fastening element on the substructure support. In an alternative embodiment of the invention, the further fastening element can be a latching element and/or further fastening elements that are considered expedient to those skilled in the art for fastening the at least one first fastening element on the substructure support.

In a further embodiment of the invention, the at least one first fastening element has an adjusting element, which is supported on the at least one first fastening element so as to be movable in the direction of the longitudinal extent of the at least one first fastening element. The adjusting element has the advantage that a position of the carrier frame, and thus also of the user interface, can be adjusted in the direction of the longitudinal extent of the at least one first fastening element. Furthermore, securing of a movement mechanism of the adjusting element, for example a nut, can be achieved in cooperation with the further fastening element of the substructure support.

The adjusting element preferably is a nut, in particular a self-locking nut, so that undesirable movements and/or changes in the position of the adjusting element with respect to the at least one first fastening element is prevented. Furthermore, the adjusting element can have flange sleeves, which are supported and/or arranged in the direction of the longitudinal extent of the at least one first fastening element before and after the nut. Stable guidance of the adjusting element on the at least one first fastening element is thereby achieved. Furthermore, advantageous sliding of the nut during adjustment of the position, in particular height, of the carrier frame can also be achieved by the flange sleeves.

The substructure support has an opening for supporting the adjusting element, wherein the opening has an extent in at least one direction, which is greater than a transverse extent of the adjusting element. Simple adjustment of a position of the carrier frame and therewith also the user interface, is achieved thereby. The adjusting element for adjustment of the position of the carrier frame can be grasped by a technician with a tool. A transverse extent of the adjusting element means the diameter of the adjusting element. The extent of the opening in the at least one direction is preferably oriented parallel to the transverse extent of the adjusting element.

In another embodiment of the invention, the at least one first fastening element has a length of at least 6 cm or at least 8 cm. or at least 10 cm. or at least 12 cm. or at least 14 cm. or at least 16 cm. or approx. 17 cm. Due to the length of the at least one first fastening element, an adjustment of the position of the carrier frame, and therewith also of the user interface, can be achieved in an assembled state of the housing shell, since the at least one first fastening element can project beyond a covering region of the housing shell.

Furthermore, the housing apparatus can have at least one second fastening element, by which the carrier frame can be fastened on the substructure support so as to be movable in at least one direction. The at least one second fastening element is preferably designed such that the carrier frame and/or the user interface is arranged on the substructure support so as to be movable in at least one direction in a fastened state of the carrier frame and/or user interface. Preferably, the at least one second fastening element is designed such that the carrier frame and/or the user interface is arranged on the substructure support so as to be movable in at least two directions in a fastened state of the carrier frame and/or user interface. The one direction, or the two directions, in which the carrier frame, and therefore the user interface, is movable when the carrier frame is fastened on the substructure support, is or are preferably oriented perpendicularly to a longitudinal extent of the at least one second fastening element. A compensating movement of the carrier frame, and therewith of the user interface, with respect to the housing shell and/or the substructure support is possible due to the movable arrangement and/or fastening of the carrier frame on the substructure support upon assembly of the housing shell. Tolerances, especially manufacturing tolerances, of the individual components, such as the user interface and/or housing shell, can be compensated in the assembly of the user interface and housing shell. An orientation of the user interface and/or housing shell, which takes account of the exact dimensions of the user interface and/or housing shell, is therefore only still partially necessary in a first assembly of the housing apparatus. By contrast, simple disassembly or assembly of the housing shell can be achieved in a service case since consideration of the exact dimensions is not necessary.

In a further embodiment of the invention, the carrier frame has at least one recess having a first diameter and the at least one second fastening element is guided through this at least one recess when the carrier frame is fastened on the substructure support, wherein the at least one second fastening element has a second diameter, which is smaller than the first diameter of the at least one recess of the carrier frame. A movable arrangement and/or fastening of the carrier frame on the substructure support can be achieved particularly easily hereby, wherein room for maneuver between the carrier frame and the substructure support can be determined from a difference between the first diameter and the second diameter. A diameter of the at least one recess of the carrier frame should here be taken to mean a maximum extension of the recess in the region of an opening area of the recess on a carrier surface of the carrier frame. The recess is preferably formed by a cylindrical hole.

Advantageously movable support of the carrier frame, and therewith also of the user interface, on the substructure support can be achieved if the second diameter of the at least one second fastening element corresponds to at least 80% of the first diameter of the at least one recess of the carrier frame. Particularly advantageously the second diameter of the at least one second fastening element corresponds to at least 70% of the first diameter of the at least one recess of the carrier frame. Particularly preferably the second diameter of the at least one second fastening element corresponds to at least 60% of the first diameter of the at least one recess of the carrier frame. Particularly preferably the second diameter of the at least one second fastening element corresponds to at least 55% of the first diameter of the at least one recess of the carrier frame. For example, the first diameter of the at least one recess of the carrier frame can be 9 mm and the second diameter of the at least one second fastening element 5 mm, so that room for maneuver for a movement, in particular a compensating movement, of the carrier frame can be achieved with respect to the at least one second fastening element and/or substructure support of ±2 mm.

Furthermore, the at least one second fastening element comprises a shoulder screw. A shoulder screw means a screw that has a screw head at a first end region and a threaded portion at a second end region and between the screw head and the threaded portion has a shoulder portion without thread. This shoulder portion preferably has a larger diameter than the diameter of the threaded portion. In the direction of the longitudinal extent of the shoulder screw, this shoulder portion can have a length that is longer than the length of the threaded portion. Mobility of the carrier frame, and therewith also of the user interface, with respect to the substructure support when the carrier frame is fastened on the substructure support, is ensured by the thread-free shoulder portion of the shoulder screw. When the carrier frame is fastened on the substructure support, this shoulder portion is preferably supported inside the at least one recess of the carrier frame, so that the carrier frame and therewith the user interface are arranged so as to be movable also with respect to the at least one second fastening element when the carrier frame is fastened on the substructure support.

In another embodiment of the invention, the substructure support has a fastening element corresponding to the at least one second fastening element, so that simple and secure fastening of the carrier frame, and therewith also of the user interface, on the substructure support is enabled. If the at least one second fastening element is formed by a screw, in particular a shoulder screw, the fastening element corresponding to the at least one second fastening element preferably has a nut and/or a threaded bushing, in particular a nut and/or threaded bushing integrated in the substructure support. A nut and/or threaded bushing integrated in the substructure support means a nut and/or threaded bushing mounted inside the substructure support so as to be secured against rotation.

Furthermore, the at least one second fastening element and the fastening element corresponding to the at least one second fastening element are screwed together as far as they will go, wherein the carrier frame is movable with respect to the substructure support. Screwed together as far as they will go here means that the at least one second fastening element, in particular the shoulder screw, and the fastening element corresponding to the at least one second fastening element, in particular the nut and/or threaded bushing integrated in the substructure, are screwed together over the entire length of a screw thread of the at least one second fastening element and/or over the entire length of the screw thread of the corresponding fastening element. For example, with a design of the second fastening element as a shoulder screw, the shoulder portion can directly rest on the fastening element corresponding to the second fastening element, or adjoin it, if the at least one second fastening element and the fastening element corresponding to the at least one second fastening element are screwed together as far as they will go. This enables particularly secure fastening of the carrier frame, and therewith also of the user interface, on the substructure support with simultaneous movable support of the carrier frame, and therewith also of the user interface, with respect to the substructure support.

Furthermore, the housing apparatus according to the invention can have a damping disk, which is arranged between the at least one second fastening element and the carrier frame. For example, the damping disk can be arranged between the screw head of the at least one second fastening element and an edge region of the carrier frame surrounding the recess. Advantageous vibration-damped support and/or fastening of the carrier frame, and therewith also of the user interface, with respect to the substructure support is achieved by the damping disk. A particularly stable and inexpensive damping disk can be achieved if the damping disk is formed of a Sylomer material, in particular special polyurethane elastomer. Furthermore, advantageous pre-tensioning between the at least one second fastening element, and therewith also the substructure support, and the carrier frame can be achieved. A frictional force between the carrier frame and the damping disk can be increased, and therefore undesirable movement of the carrier frame can be prevented by the damping disk, in particular the pre-tensioned damping disk. Purposeful adjustment of the pre-tensioning can ensure mobility of the carrier frame for a compensating movement with respect to the substructure support. Furthermore, the damping disk and/or the pre-tensioning generated by the damping disk can have the function of a screw fastening. The damping disk is designed to be self-adhesive on at least one surface, so that it sticks to the screw head of the at least one second fastening element and/or a further component, for example a flat washer. Furthermore the diameter of a middle opening region for mounting of the at least one second fastening element can be smaller than the diameter of the at least one second fastening element, so that the damping disk is captively supported on the second fastening element upon assembly of the second fastening element. For example, the hole diameter of the damping disk can be 4 mm and the diameter of the at least one second fastening element 5 mm. Assembly of the at least one second fastening element can be simplified significantly thereby. The at least one second fastening element can be assembled in a particularly time-saving manner.

The housing apparatus can have a large diameter washer, on which the damping disk is arranged. A large diameter washer here means a flat washer that has an external diameter that essentially corresponds to two times, preferably three times, the hole diameter of the flat washer. This enables advantageous and secure fastening of the carrier frame by the at least one second fastening element on the substructure support with simultaneous mobility of the carrier frame, and therewith also of the user interface, with respect to the substructure support.

For secure and durable fastening of the user interface on the substructure support, the housing apparatus has more than one second fastening element. The housing apparatus can have two second fastening elements, and preferably has three second fastening elements and more preferably the housing apparatus has four second fastening elements and the carrier frame also has four recesses, wherein each of the four recesses is provided for mounting one of the four second fastening elements.

In another embodiment of the invention, the carrier frame has at least one first centering element and the housing shell has at least one second centering element, which is designed so as to correspond to the at least one first centering element of the carrier frame. The first centering element and the second centering element are coordinated such that when the two centering elements mesh, the user interface is arranged exactly inside an opening of the housing shell. Uniform optical gaps can be achieved on a surface visible to the user between the housing shell and user interface, in particular the communication circuit of the user interface.

The at least one first centering element of the carrier frame preferably has a slot, so that room to maneuver is provided for a tolerance compensation in the direction of a longitudinal extent of the slots during assembly of the housing shell.

The at least one first centering element, in particular the slot, has a longitudinal extent, oriented parallel to the longitudinal extent of the at least one first fastening element. This has the advantage that an exact orientation and/or adjustment of the carrier frame, and therewith also of the user interface, can occur in the direction of the longitudinal extent of the at least one first fastening element by the at least one first fastening element, in particular by the adjusting element of the at least one first fastening element, even after assembly of the housing shell on the substructure support. Furthermore, a possibility for compensating manufacturing tolerances on and/or after assembly of the housing shell on the substructure support is provided in this way.

In a further embodiment of the invention, the at least one second centering element of the at least one housing shell is conical, so that the at least one second centering element can easily fit and/or engage in the at least one first centering element on assembly of the housing shell on the substructure support.

The housing shell can have at least one opening inside in which the user interface is arranged when the housing shell is arranged on the substructure support. This enables integration of the user interface inside a surface of the housing shell. When the housing shell is arranged on the substructure support, the housing shell and the user interface can form a shared flat surface. This also allows simple cleaning of the housing apparatus, and this is very advantageous with use inside a medical imaging apparatus. The flat surface can be a level surface.

Furthermore, the invention encompasses a medical imaging apparatus having a scanner provided with a housing apparatus, wherein the housing apparatus has at least one housing shell, a substructure support, on which the at least one housing shell is fastened, and a user interface having a carrier frame and a communication circuit. The carrier frame is arranged on the substructure support so as to be movable in at least one direction.

A medical imaging apparatus designed in this way has the advantage of simple assembly of the housing apparatus with an integrated user interface. This enables simple and fast integration of the user interface inside the housing apparatus. Upon final assembly of the housing shell, a compensating movement of the carrier frame, and therewith also of the user interface, with respect to the housing shell and/or the substructure support is possible due to the movable arrangement of the carrier frame on the substructure support. The compensating movement is a movement that the carrier frame experiences upon assembly of the housing shell on the substructure support, so the user interface, in particular the communication circuit of the user interface, is placed inside the opening of the housing shell. Tolerances, especially manufacturing tolerances, of the individual components can be compensated thereby during assembly of the user interface and the housing shell. Time-consuming individual handling and/or orientation of the user interface and/or housing shell, in order to take account of the exact and/or individual dimensions of the user interface and/or housing shell, in the assembly of the housing apparatus is therefore no longer required. This is also true in the case of a service call, in which the housing apparatus has to be disassembled, because the simple and fast disassembly and assembly of the housing shell is provided for the service engineer.

The advantages of the inventive medical imaging apparatus essentially correspond to the advantages of the inventive housing apparatus, which have been described above in detail. Features, advantages or alternative embodiments mentioned in this context are applicable to the apparatus as well.

DESCRIPTION OF THE PREFERRED EMBODIMENTS

Figure 1:
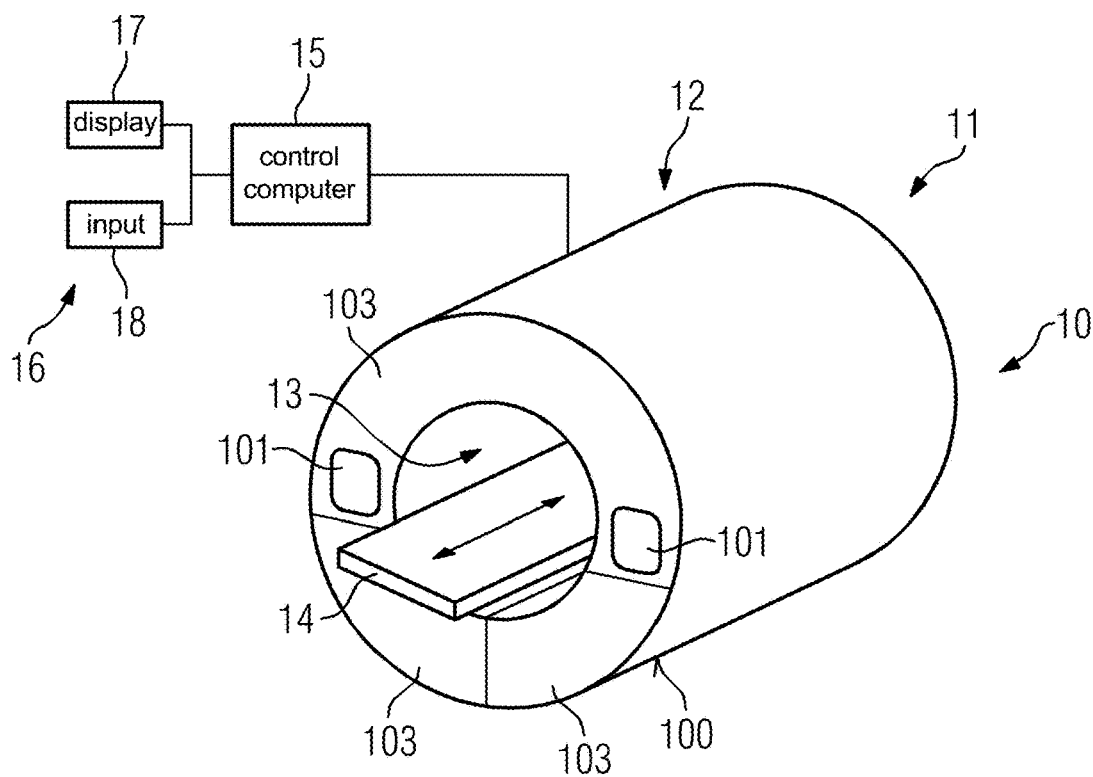
FIG. 1 schematically illustrates an inventive medical imaging apparatus.

FIG. 1 schematically shows a medical imaging apparatus. In the exemplary embodiment, the medical imaging apparatus is a magnetic resonance apparatus 11. The present invention is not restricted to the embodiment of the medical imaging apparatus as a magnetic resonance apparatus 11, however, and further embodiments of the medical imaging apparatus can be, for example, a computed tomography apparatus, a PET apparatus, etc.

The magnetic resonance apparatus 11 has a magnetic resonance data acquisition scanner 12 that has a superconducting basic field magnet (not shown) that generates a strong and constant basic magnetic field. The scanner 12 also has a gradient coil arrangement and a radio-frequency (RF) antenna. Furthermore, the scanner 12 has a patient-receiving region 13 for receiving a patient. In the exemplary embodiment, the patient-receiving region 13 is cylindrical and is circumferentially surrounded by the scanner 12. A different design of the patient-receiving region 13 is conceivable, however. A patient can be pushed and/or moved into the patient-receiving region 13 by a patient-positioning device 14 of the scanner 12. The magnetic resonance apparatus 11 also has a housing apparatus 100, which surrounds the scanner 12.

For controlling the magnetic resonance apparatus 11, the magnetic resonance apparatus 11 has a system control computer 15. The system control computer 15 centrally controls the magnetic resonance apparatus 11, such as carrying out a predetermined imaging gradient echo sequence. Furthermore, the system control computer 15 includes an evaluation processor (not shown) for evaluation of medical image data, which are acquired by the scanner 12 during the magnetic resonance examination.

Furthermore, the magnetic resonance apparatus 11 has a first user interface 16, which is connected to the system control computer 15 and is arranged inside a control room and/or control center. The first user interface 16 is therefore spatially separated from the scanner 12 and also separate from the housing apparatus 100 of the scanner 12. Control information, such as, for example, imaging parameters, and reconstructed magnetic resonance images can be displayed on a display unit 17, for example on at least one monitor, of the user interface 16 for a medical operator. The user interface 16 also has an input unit 18 via which information and/or parameters can be entered by the medical operator during a scanning procedure.

Figure 2:
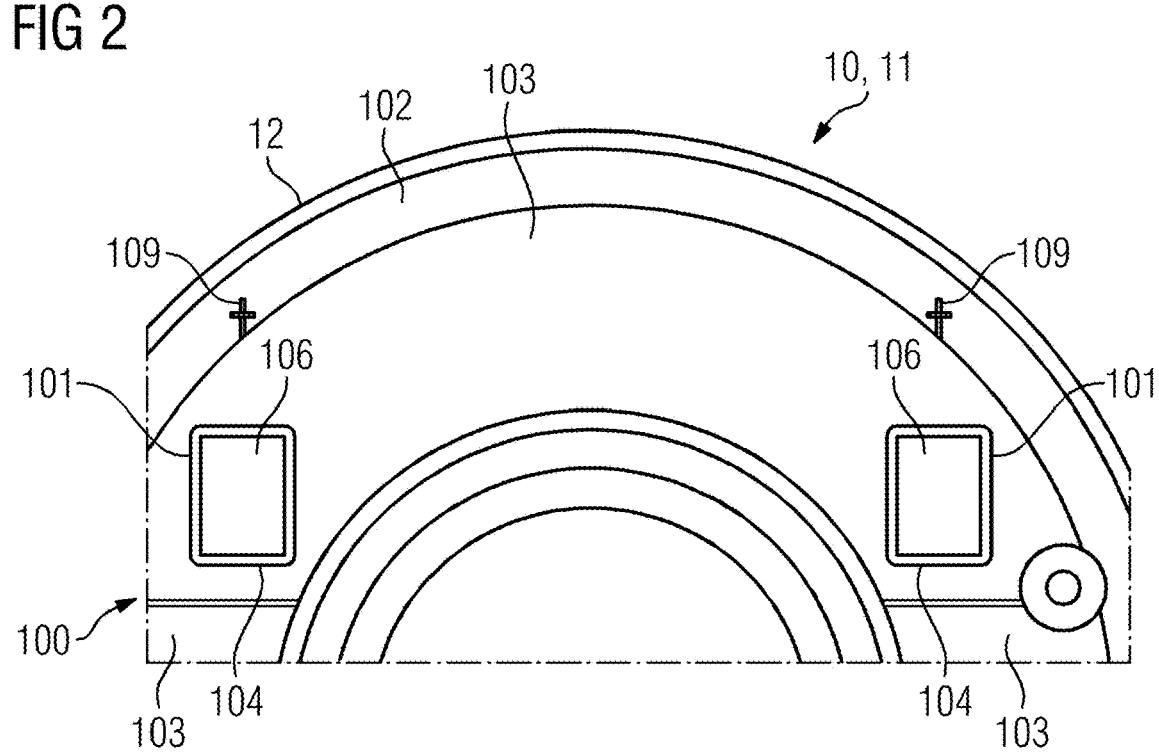
FIG. 2 shows a housing shell according to the invention having two integrated user interfaces, in a front view.

The medical imaging apparatus, in the exemplary embodiment the magnetic resonance apparatus 11, also has at least one further user interface 101, which is integrated inside the housing apparatus 100 of the magnetic resonance apparatus 11. In the exemplary embodiment, the magnetic resonance apparatus 11 has two user interfaces 101, which are integrated inside the housing apparatus 100 (FIGS. 1 and 2). In an alternative embodiments of the invention, the magnetic resonance apparatus 11 can have just a single user interface 101, or more than two user interfaces 101, which are integrated inside the housing apparatus 100.

The housing apparatus 100 has a substructure support 102 and a number of housing shells 103. The substructure support 102 is arranged on the scanner 12. The housing shells 103 are arranged and/or fastened on the scanner 12 by the substructure support 102. In the exemplary embodiment, the housing apparatus 100 has three housing shells 103 on a front side of the scanner 12, and these include an upper half ring and two lower quarter rings (FIGS. 1 and 2). Furthermore, the housing apparatus 100 has the two user interfaces 101, which are arranged inside the housing shell 103 of the housing apparatus 100 designed as an upper half ring. For this purpose, the housing shell 103 designed as an upper half ring has two recesses 104, wherein one of these two recesses 104 respectively is designed for an arrangement of one of the two user interfaces 101 if the respective user interface 101 is arranged and/or fastened on the substructure support 102. The housing shell 103 designed as the upper half ring and the two user interfaces 101, in particular a display surfaces of the two user interfaces 101, form a flat surface.

The two user interfaces 101 have a similar design, so that construction and arrangement and/or fastening of the two user interfaces 101 will be described and illustrated below with reference to a single user interface 101. Construction and arrangement and/or fastening of the further user interface 101 of the two user interfaces 101 occurs analogously.

Figure 3:
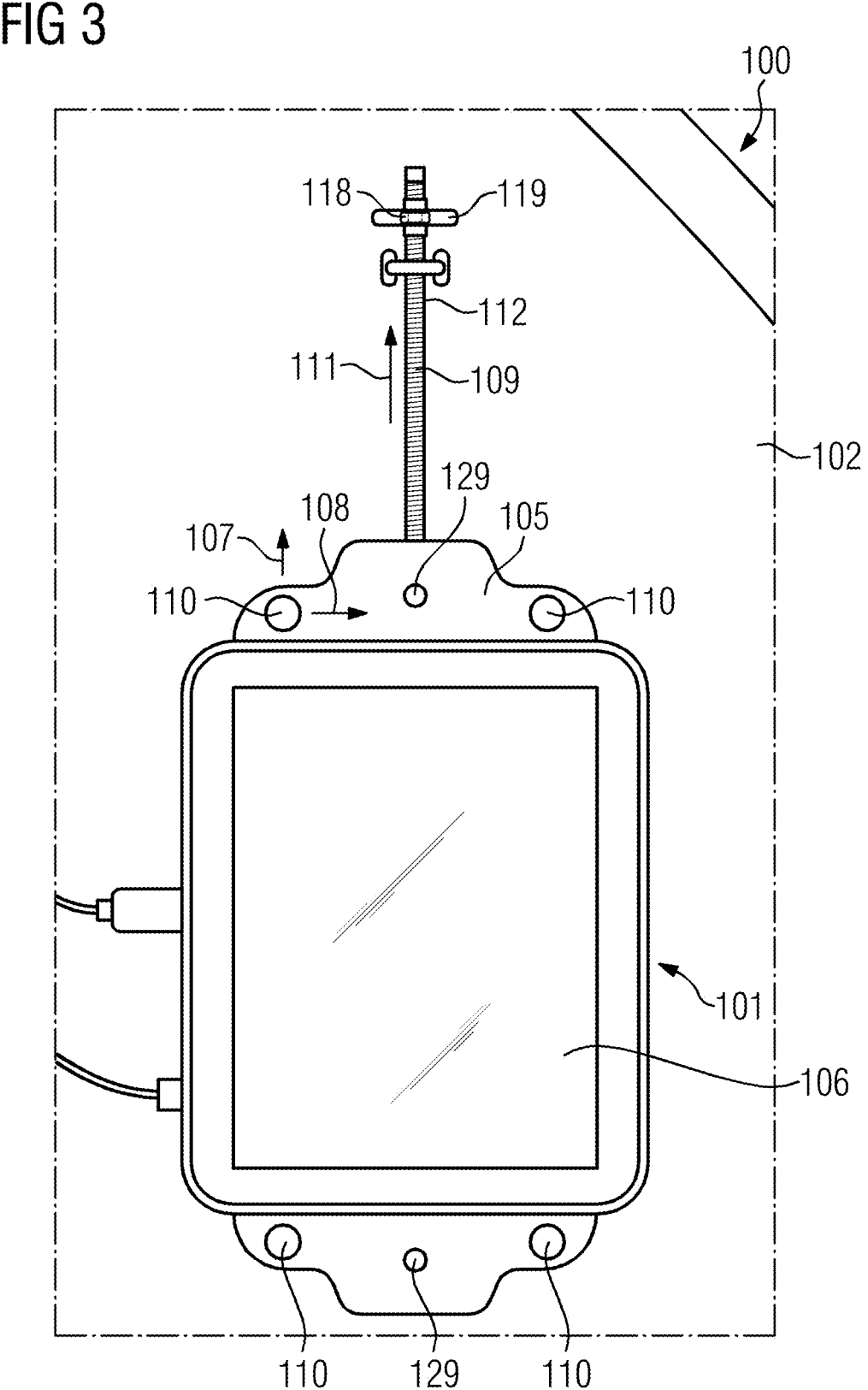
FIG. 3 shows in a front view the user interface according to the invention when arranged on the substructure support.
Figure 6:
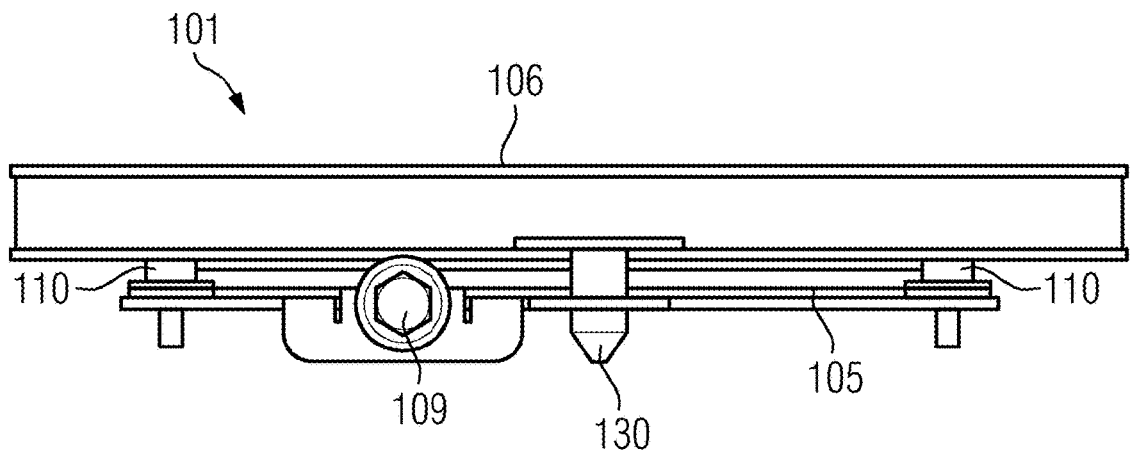
FIG. 6 shows a side view of the user interface according to the invention.

The user interface 101 has a carrier frame 105 and a communication circuit 106 (FIGS. 3 and 6). In the present exemplary embodiment, the carrier frame 105 and the communication circuit 106 form a shared structural unit. In an alternative embodiment of the invention, the carrier frame 105 can also have a structural unit separate from the communication circuit 106. The communication circuit 106 is arranged on a surface of the carrier frame 105 remote from the scanner 12. In the exemplary embodiment, the communication circuit 106 is a touch display, via of which information can be displayed and/or represented for a user and a user can make inputs directly on a display surface. In an alternative embodiment of the invention, the communication circuit 106 can also perform just one function for representation of information, such as with the communication circuit 106 being designed as a display or as a monitor, or also just one function for an input of information, such as the communication circuit 106 being designed as a keyboard and control panel.

The carrier frame 105 is designed for fastening the user interface 101, in particular the communication circuit 106, on the housing apparatus 100 (FIG. 3). For this purpose, the carrier frame 105 is arranged and/or fastened on the substructure support 102, wherein the carrier frame 105 is arranged and/or fastened on the substructure support 102 so as to be movable in at least one direction 107, 108, preferably in two directions 107, 108, for this purpose. In particular, the carrier frame 105 is provided for assembly of the housing shell 103, in particular of the housing shell 103 designed as a half ring, on the substructure support 102 for a compensating movement with respect to the substructure support 102 and/or housing shell 103.

Figure 4:
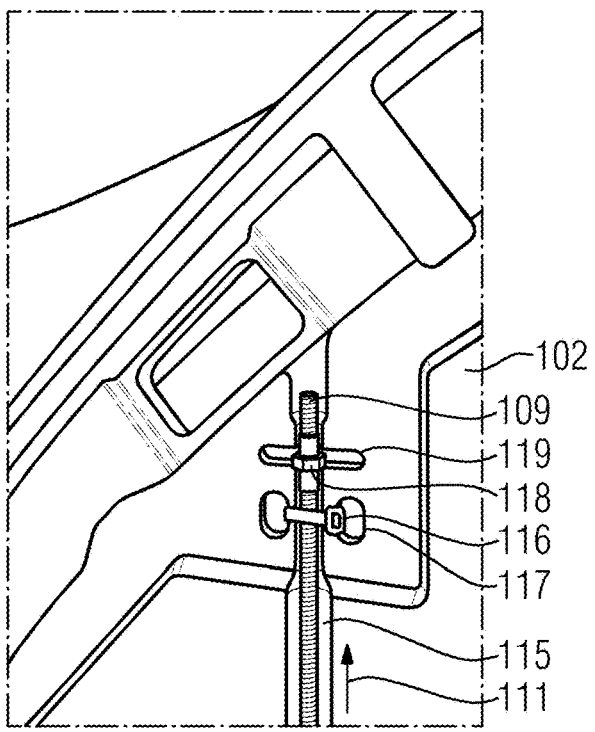
FIG. 4 shows a first fastening element on the substructure support according to the invention.
Figure 7:
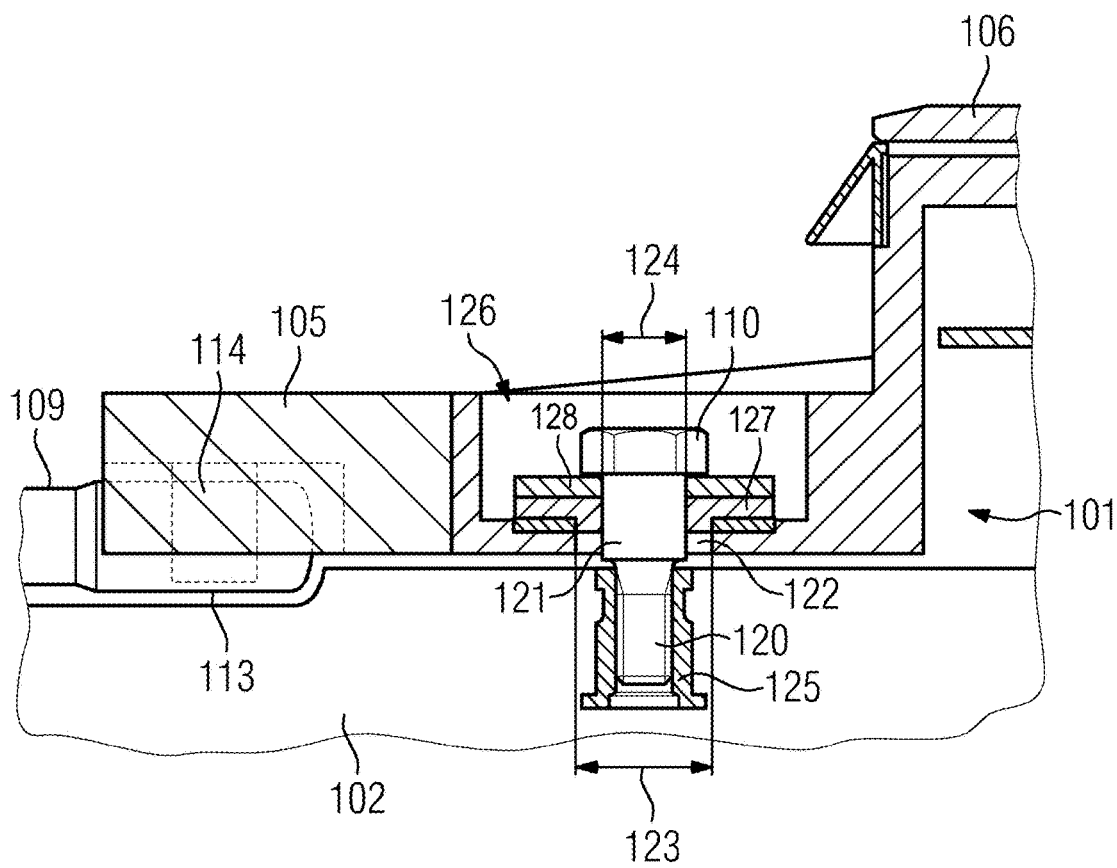
FIG. 7 shows the user interface according to the invention having a second fastening element in a sectional view.

For this purpose, the housing apparatus 100 has a number of fastening elements 109, 110. A first fastening element 109 of the housing apparatus 100 is provided for pendulum-like support of the carrier frame 105 on the substructure support 102 (FIGS. 3, 4 and 7). For this purpose, the first fastening element 109 is formed by an eyebolt in the present exemplary embodiment. The eyebolt is a screw, which in the direction 111 of its longitudinal extent has a thread at a first end region and in the direction 111 of its longitudinal extent has a ring 113 at a second end region. The first end region and the second end region are at opposing end regions of the eyebolt. The ring 113 of the eyebolt encompasses a ring surface, wherein a surface normal of the ring surface is oriented perpendicularly to the longitudinal extent of the eyebolt.

The first fastening element 109, in particular the eyebolt, has a length of at least 6 cm. or a length of at least 8 cm. or a length of at least 10 cm. or a length of at least 12 cm. or a length of at least 14 cm. or a length of at least 16 cm or a length of approx. 17 cm.

Figure 5:
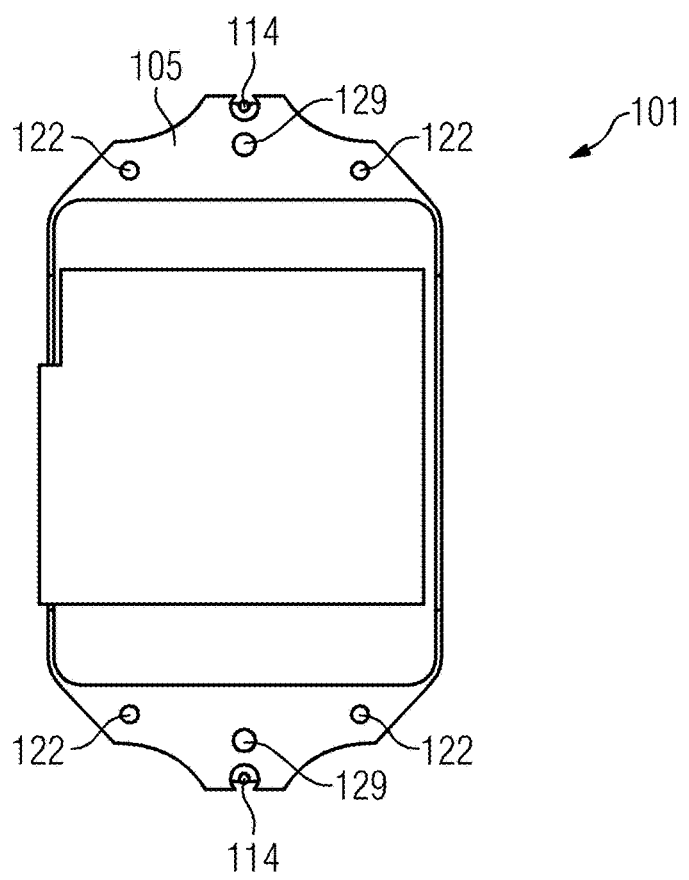
FIG. 5 shows the user interface according to the invention in a rear view.

For pendulum-like support of the carrier frame 105 on the substructure support 102 the carrier frame 105 has a support element 114 (FIGS. 5 and 7). The support element 114 is arranged on the back side or rear side of the carrier frame 105 essentially perpendicularly to a back side or rear side of the carrier frame 105. The support element of the carrier frame 105 is designed to be cone-like and/or rod-like. The first fastening element 109 also has a support element, which is designed to correspond to the support element of the carrier frame 105. In the present exemplary embodiment, the support element of the first fastening element 109 includes the ring 113 of the eyebolt. If the support element 114, in particular the extension-like and/or cone-like support element 114, of the carrier frame 105 is supported inside the support element of the first fastening element 109, in particular inside the ring 113 of the eyebolt, then the carrier frame 105 is also supported on the eyebolt and the carrier frame 105 is therewith also supported pendulum-like on the substructure support 102.

In the exemplary embodiment, the carrier frame 105 has two support elements 114, in particular the extension-like and/or cone-like support element 114, wherein one of the support elements 114 respectively is arranged at an end region. The two end regions are arranged at opposing edge regions of the carrier frame 105 on the back side of the carrier frame 105, moreover. The user interface 101 has two preferred mounting positions and can be fitted or arranged inside the housing apparatus in a first mounting position as well as in a second mounting position, which is rotated by 180° with respect to the first mounting position.

For fastening and/or arrangement of the first fastening element 109 on the substructure support 102 the substructure support 102 has an indentation 115, in which the first fastening element 109 is supported (FIG. 4). The indentation 115 has a longitudinal extent which has at least one longitudinal extent of the first fastening element 109, in particular the eyebolt, so that the entire first fastening element 109 can be compactly supported inside the indentation 115 of the substructure support 102. Furthermore, the substructure support 102 also has a further fastening element 116 which fastens the first fastening element 109, in particular the eyebolt, inside the indentation 115. In the present exemplary embodiment, the further fastening element 116 is formed by a cable tie, which is also arranged in recesses 117 and/or holes in the substructure support 102.

The first fastening element 109 has an adjusting element 118 by which a position can be adjusted in the direction 111 of the longitudinal extent of the first fastening element 109 (FIGS. 3 and 4). For this purpose, the adjusting element 118 is moveably supported on the first fastening element 109. The adjusting element 118 is a nut having sliding bushes and/or flange sleeves mounted in front and behind, so that the adjusting element 118 is moveably and stably supported along the longitudinal extent of the first fastening element 109. The adjusting element 118 preferably is a self-locking nut, so that an undesirable movement or change in position of the nut with respect to the at least one first fastening element 109 can advantageously be prevented. In particular, only desired movements and/or changes in position can be carried out by a technician in this way.

The substructure support 102 also has an opening 119 for mounting the adjusting element 118. The opening 119 for mounting the adjusting element 118 has a longitudinal extent, which is oriented essentially transversely to the longitudinal extent of the indentation 115 for mounting and/or supporting the first fastening element 109. Furthermore, the longitudinal extent of the opening 119 for mounting the adjusting element 118 is greater than a transverse extension of the adjusting element 118. Due to the opening 119 for mounting the adjusting element 118, the adjusting element 118 can be grasped by a user and/or a tool for adjusting a position of the carrier frame 105, and therewith a position of the user interface 101, in the direction 111 of the longitudinal extent of the first fastening element 109. By rotating the adjusting element 118 with respect to the first fastening element 109, the first fastening element 109 changes its position inside the indentation 115 for mounting the first fastening element 109, and therewith with respect to the substructure support 102, since a position of the adjusting element 118 is fixed with respect to the substructure support 102 owing to the opening 119 for mounting the adjusting element 118.

For fastening the carrier frame 105, and therewith also the user interface 101, on the substructure support 102, the housing apparatus 100 has at least one second fastening element 110 (FIGS. 3, 6 and 7). In the exemplary embodiment, the housing apparatus 100 has four second fastening elements 110. By means of the second fastening elements 110 the carrier frame 105, and therewith also the user interface 101, is moveably fastened on the substructure support 102. In the present exemplary embodiment, the second fastening elements 110 are formed by shoulder screws. The shoulder screws comprise a first end region having a screw head and having a threaded portion 120 at a second end region, wherein a shoulder portion 121 without thread is arranged between the screw head and the threaded portion 120. This shoulder portion 121 preferably has a greater diameter than a diameter of the threaded portion 120. In the direction of a longitudinal extent of the shoulder screw, this shoulder portion 121 can have a length, which is longer than a length of the threaded portion 120. In the present exemplary embodiment, the diameter of the shoulder portions 121 of the shoulder screws is 5 mm, while the threaded portions 120 are formed by M4 threads.

The carrier frame 105 has four recesses 122 for this purpose, with one of the four recesses 122 respectively being designed for mounting one of the four second fastening elements 110. The four recesses 122 each have a first diameter 123 and the four second fastening elements 110, in particular the shoulder portions 121 of the shoulder screws, each have a second diameter 124, with the second diameter 124 of the second fastening elements 110 being smaller than the first diameter 123 of the recesses 122 of the carrier frame 105. The second diameter 124 of the second fastening elements 110 corresponds to at least 80% of the first diameter 123 of the recesses 122 of the carrier frame 105. The second diameter 124 of the second fastening elements 110 corresponds to at least 70% of the first diameter 123 of the recesses 122 of the carrier frame 105. The second diameter 124 of the second fastening elements 110 corresponds to at least 60% of the first diameter 123 of the recesses 122 of the carrier frame 105. The second diameter 124 of the second fastening elements 110 corresponds to at least 55% of the first diameter 123 of the recesses 122 of the carrier frame 105. In the exemplary embodiment, the first diameter 123 of the recesses 122 of the carrier frame 105 is 9 mm and the second diameter 124 of the second fastening elements 110 is 5 mm. The second fastening elements 110 are arranged inside the recesses 122 of the carrier frame 105 in such a way that the shoulder portions 121 are supported inside the recesses 122. This enables a movement of the carrier frame 105 with respect to the second fastening elements 110 and/or the substructure support 102 of ±2 mm.

For fastening the carrier frame 105 on the substructure support 102, the substructure support 102 also has fastening elements 125, which are designed to correspond to the second fastening elements 110, in particular to the threaded portions 120 of the shoulder screws (FIG. 7). In the exemplary embodiment, these corresponding fastening elements 125 are formed by threaded bushing or nuts integrated in the substructure support 102. These threaded bushing or nuts integrated in the substructure support 102 are arranged inside the substructure support 102 such that they are arranged inside the substructure support 102 so as to be secured against rotation.

The carrier frame 105 also has four indentations 126, with one indentation respectively being arranged around one of the four recesses 122 for mounting a second fastening element 110 respectively (FIG. 7). In particular, one of the four recesses 122 respectively is arranged in one of the four indentations 126 respectively for mounting a second fastening element 110. When the carrier frame 105 is fastened on the substructure support 102, the screw heads of the four fastening elements 110 are supported in these indentations 126 of the carrier frame 105. As a result, the second fastening elements 110 do not project from the indentations 126, so that undesirable hindering by to the second fastening elements 110 on further assembly is prevented. The screw heads have a diameter which is greater than a diameter of the recesses 122, in which the shoulder portions of the shoulder screws are supported, of the carrier frame 105.

The housing apparatus 100 also has four damping disks 127, which are arranged between the second fastening elements 110 and the carrier frame 105, in particular edge regions of the carrier frame 105 arranged around the recesses 122. The four damping disks 127 are each formed by a Sylomer material. Furthermore, the housing apparatus 100 has four large diameter washers 128, with one of the large diameter washers 128 respectively being arranged on one of the damping disks 127. The large diameter washers 128 are each formed by flat washers. In the present exemplary embodiment, the four damping disks 127 on one side respectively, in particular on the side facing the large diameter washer 128 respectively, are self-adhesive, so that one of the large diameter washers 128 and one of the damping disks 127 respectively can be fitted together as one unit on assembly of the housing apparatus 100.

Furthermore, the damping disks 127 each have a central recess and/or a central hole in which one second fastening element 110 respectively, in particular the shoulder portion 121 of the shoulder screws, is guided and/or supported. In the present exemplary embodiment, these central recesses and/or central holes of the damping disks 127 have a hole diameter of 4 mm so a frictional force between the damping disks 127 and second fastening elements 110, in particular the shoulder portions 121 of the shoulder screws, is greater than a weight force of the damping disks 127 together with the large diameter washers 128. As a result, the damping disks 127, together with the large diameter washers 128, can be captively supported on the second fastening elements 110, in particular on the shoulder portions 121 of the shoulder screws, for assembly of the second fastening elements 110 on the carrier frame 105 and the substructure support 102.

The second fastening elements 110, in particular the shoulder screws, are screwed as far as they will go to the corresponding fastening elements 125, in particular the nuts and/or threaded bushes integrated in the substructure support 102. This means that the second fastening elements 110, in particular the shoulder screws, are screwed together to the corresponding fastening elements 125, in particular the nuts and/or threaded bushes integrated in the substructure 102, along the entire length of a screw thread of the second fastening elements 110 and/or along the entire length of a screw thread of the corresponding fastening elements 110. As a result, one shoulder portion 121 respectively of one of the second fastening elements, in particular the shoulder screws, is located on one of the corresponding fastening elements 125, in particular the nuts and/or threaded bushes integrated in the substructure 102.

Due to the damping elements 127 and large diameter washers 128 arranged between the borders of the recesses 122 of the carrier frame 105 and the second fastening elements 110, in particular the screw heads of the shoulder screws, the second fastening elements 110 are arranged with pre-tensioning on the substructure support 102. The carrier frame 105, and therefore also the user interface 101, are thereby also arranged with pre-tensioning on the substructure support 102. Pre-tensioning also achieves advantageous vibration damping of the carrier frame 105 and therewith also of the user interface 101 with respect to the substructure support 102. As a result, independent movement of the carrier frame 105, and therewith also of the user interface 101, with respect to the substructure support 102 is advantageously prevented without the action of an external force, so that an adjusted position of the carrier frame 105, and therewith also of the user interface 101, is prevented.

If an outer force does act, as is the case during assembly of the housing shell 103 designed as a half ring on the substructure support 102, on the carrier frame 105, the embodiment of the second fastening elements 110 and the recesses 122 of the carrier frame 105 designed for mounting the second fastening elements 110 enables a movement of the carrier frame 105 and therewith also of the user interface 101 with respect to the substructure support 102. Therefore, the carrier frame 102, and therewith also the user interface 101, remain movable with respect to the substructure support 102 even when the carrier frame 105 is fastened on the substructure support 102. Room for maneuver of the carrier frame 105, and therewith also of the user interface 101, with respect to the substructure support 101 is therefore limited to ±2 mm due to the construction. An effective compensating movement of the carrier frame 105, and therewith also of the user interface 101, with respect to the substructure support 102 is enabled thereby in the assembly of the housing shell 103 designed as a half ring. In an alternative embodiment of the invention, in particular in an alternative embodiment of the shoulder screws and recesses 122 of the carrier frame 105, room for maneuver can also be greater than ±2 mm or even less than ±2 mm.

For simple assembly and simple and effective adjustment of a compensating movement on assembly of the housing shell 103 designed as a half ring, the carrier frame 105 has at least one first centering element 129. The first centering element 129 has a slot of the carrier frame 105. Furthermore, the first centering element 129 designed as a slot has a longitudinal extent, which is formed parallel to the first fastening element 109, in particular the longitudinal extent of the first fastening element 109, so that a compensating movement of the carrier frame 105, and therewith also of the user interface 101, with respect to the housing shell 103 designed as a half ring is enabled.

The housing shell 103 also has a second centering element 130 for this purpose, which is designed to correspond to the first centering element 129 of the carrier frame 105. The second centering element 130 is preferably conical, so that on assembly of the housing shell 103 designed as a half ring, the two centering elements 129, 130 can advantageously mesh. Preferably the first centering element 129 and the second centering element 130 are coordinated in such a way that on meshing of the two centering elements 129, 130, the user interface 101 is arranged exactly inside an opening 104 in the housing shell 103. In particular, uniform optical gaps can be achieved here on a surface visible to the user between the housing shell 103 and the user interface 101, in particular the communication circuit 106 of the user interface 101. The substructure support 102 also has an indentation in which the second centering element 130 is supported if the housing shell 103 is mounted on the substructure support 102 and the second centering element 130 of the housing shell 103 projects through the first centering element 129 of the carrier frame 105.

In the exemplary embodiment, the carrier frame 105 has two centering elements 129, in particular two centering elements 129 designed as slots, with one of the centering elements 114 respectively being arranged at an end region. The two end regions are arranged, moreover, at opposing edge regions of the carrier frame 105 on the back side of the carrier frame 105. As a result, the user interface 101 has two preferred mounting positions and can be fitted and/or arranged inside the housing apparatus in a first mounting position as well as in a second mounting position, which is rotated by 180° with respect to the first mounting position.

The two centering elements 129 are arranged one a line with the two support elements 114 of the carrier frame 105. The two support elements 114 are arranged at one outer edge region respectively of the carrier frame 105 and the two centering elements 129 in an inner edge region of the carrier frame 105. Hindering of mounting and/or assembly of the housing shell 103 designed as a half ring by the support element 114 of the carrier frame 105 and/or the first fastening element 109 can advantageously be prevented hereby.

As soon as the housing shell 103 is mounted on the substructure support 102, only one position of the carrier frame 105 can then be adjusted in the direction 111 of the longitudinal extent of the first fastening element 109. For this purpose, the first fastening element 109, owing to its length, projects over a covering region of the housing shell 103 designed as a half ring, as can be seen in FIG. 2.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A housing apparatus for a medical imaging apparatus, said housing apparatus comprising:
at least one housing shell;
a substructure support on which said at least one housing shell is fastened, the substructure support including an indentation that extends in at least one direction, and an opening in the indentation, wherein the opening extends through the substructure support in a second direction transverse to the at least one direction; and
a user interface comprising a carrier frame and a communication circuit, said carrier frame being connected to said substructure support by: (a) at least one fastening element that extends in the at least one direction, and (b) an adjusting element adjustably connected to the at least one fastening element, the at least one fastening element and the adjusting element being accommodated in the indentation and the opening, wherein the adjusting element is accommodated in the opening such that the adjusting element is fixed in the at least one direction by the opening, the adjusting element being configured to be movable with respect to the at least one fastening element such that the at least one fastening element moves through the adjusting element to move the carrier frame in the at least one direction.

2. The housing apparatus as claimed in claim 1 wherein said carrier frame is configured to compensate for movement with respect to at least one of the substructure support and the housing shell, during assembly of the housing shell on the substructure support.

3. The housing apparatus as claimed in claim 1 wherein the at least one fastening element is configured to provide a pendulum-like support of the carrier frame on the substructure support.

4. The housing apparatus as claimed in claim 3 wherein said at least one fastening element is an eyebolt.

5. The housing apparatus as claimed in claim 3 wherein said carrier frame comprises at least one first support element and wherein said at least one fastening element comprises a second support element corresponding to the first support element, with said carrier frame being supported on said at least one fastening element by the respective support elements.

6. The housing apparatus as claimed in claim 3 wherein said at least one fastening element is supported in the indentation.

7. The housing apparatus as claimed in claim 3 wherein said substructure support comprises at least one further fastening element that fastens said at least one fastening element to said substructure support.

8. The housing apparatus as claimed in claim 3 wherein the adjusting element is supported on said at least one fastening element and is configured to be movable along a longitudinal extent of said at least one fastening element.

9. The housing apparatus as claimed in claim 8 wherein said opening comprises an extent transverse to the at least one direction and the second direction that is larger than: an extent of the opening in the at least one direction, and a transverse extent of said adjusting element.

10. The housing apparatus as claimed in claim 1 wherein:
the at least one fastening element is configured to provide a pendulum-like support of the carrier frame on the substructure support; and the housing apparatus further comprises a second fastening element that fastens the carrier frame on the substructure support so as to be movable in said at least one direction.

11. The housing apparatus as claimed in claim 10 wherein said carrier frame has a recess therein having a first diameter, and wherein said second fastening element is guided through said recess when said carrier frame is fastened on the substructure support, said second fastening element having a second diameter that is smaller than said first diameter.

12. The housing apparatus as claimed in claim 11 wherein said second diameter is at least 80% of said first diameter.

13. The housing apparatus as claimed in claim 11 wherein said second fastening element is a shoulder screw.

14. The housing apparatus as claimed in claim 11 wherein said substructure support comprises a substructure support fastening element that meets with said second fastening element.

15. The housing apparatus as claimed in claim 14 wherein said substructure support fastening element is integrated in the substructure support, and is selected from the group consisting of a nut and a threaded bushing.

16. The housing apparatus as claimed in claim 15 wherein said second fastening element and said substructure support fastening element are screwed together as far as they will engage while maintaining said carrier frame movable with respect to said substructure support.

17. The housing apparatus as claimed in claim 16 comprising a damping disk between said second fastening element and said carrier frame.

18. The housing apparatus as claimed in claim 17 wherein said damping disk is comprised of Sylomer material.

19. The housing apparatus as claimed in claim 17 comprising a washer on which said damping disk is situated, said washer having a larger diameter than said damping disk.

20. The housing apparatus as claimed in claim 10 wherein said carrier frame comprises four recesses, and comprising a respective second fastening element in each of said recesses.

21. The housing apparatus as claimed in claim 1 wherein said carrier frame comprises a first centering element and said housing shell comprises a second centering element that corresponds with said first centering element so as to center said carrier frame with respect to said housing shell.

22. The housing apparatus as claimed in claim 21 wherein said first centering element is a slot in said carrier frame.

23. The housing apparatus as claimed in claim 21 wherein said first centering element has a longitudinal extent that is parallel to a longitudinal extent of said at least one fastening element.

24. The housing apparatus as claimed in claim 22 wherein said second centering element is conical in shape and fits into said slot.

25. The housing apparatus as claimed in claim 1 wherein said housing shell comprises a further opening in which said user interface is received and situated.

26. The housing apparatus as claimed in claim 1 wherein, when said housing shell is situated in said substructure support, said housing shell and said user interface comprise a shared flat surface.

27. The housing apparatus as claimed in claim 1 wherein the adjusting element is configured to rotate about the at least one fastening element such that the adjusting element rotates about an axis that extends along the at least one fastening element and in the at least one direction, the rotation of the adjusting element causing the at least one fastening element to move through the adjusting element to move the carrier frame in the at least one direction.

28. The housing apparatus as claimed in claim 1 wherein the opening allows access to the adjusting element by a user to facilitate manipulation, via and extending through the opening, of the adjusting element by the user to cause the least one fastening element to move through the adjusting element to move the carrier frame in the at least one direction.

29. The housing apparatus as claimed in claim 1 wherein the substructure support further comprises:
first and second openings through the substructure support that are spaced from the opening in the at least one direction, the first and second openings being located on opposing sides of the indentation in a third direction transverse to the at least one direction and the second direction; and
a second fastening element that fastens the at least one fastening element in the indentation, the second fastening element being configured to engage the first and the second openings, and to extend between the first and second openings in the third direction.

30. A medical imaging apparatus comprising:
a medical image data acquisition scanner comprising a housing apparatus, wherein said housing apparatus comprises:
at least one housing shell,
a substructure support on which said at least one housing shell is fastened, the substructure support including an indentation that extends in at least one direction, and an opening in the indentation, wherein the opening extends through the substructure support in a second direction transverse to the at least one direction, and
a user interface comprising a carrier frame and a communication circuit, said carrier frame being connected to said substructure support by: (a) at least one fastening element that extends in the at least one direction, and (b) an adjusting element adjustably connected to the at least one fastening element, the at least one fastening element and the adjusting element being accommodated in the indentation and the opening, wherein the adjusting element is accommodated in the opening such that the adjusting element is fixed in the at least one direction by the opening, the adjusting element being configured to be movable with respect to the at least one fastening element such that the at least one fastening element moves through the adjusting element to move the carrier frame in the at least one direction.

* * * * *